United States Patent [19]

Babil et al.

[11] 4,246,640
[45] Jan. 20, 1981

[54] AUTOMATIC RECORDER ABSCISSA SCALING

[75] Inventors: Simon Babil, Trumbull; Andrew R. Muir, Wilton, both of Conn.

[73] Assignee: The Perkin-Elmer Corporation, Norwalk, Conn.

[21] Appl. No.: 15,087

[22] Filed: Feb. 26, 1979

[51] Int. Cl.³ .............................................. G01D 9/26
[52] U.S. Cl. .................................. 364/520; 364/557; 346/134
[58] Field of Search ............... 364/520, 557; 346/134, 346/140 R, 33 TP, 25, 65; 73/343.5

[56] References Cited

U.S. PATENT DOCUMENTS

| | | | |
|---|---|---|---|
| 3,555,254 | 1/1971 | Gerber | 364/520 X |
| 3,636,314 | 1/1972 | Kan et al. | 364/520 |
| 3,753,369 | 8/1973 | Fowler et al. | 73/343.5 X |
| 3,795,007 | 2/1974 | Mohrman et al. | 346/134 X |
| 3,826,140 | 7/1974 | Nakagawa et al. | 73/343.5 |
| 3,879,604 | 4/1975 | Malmvig | 364/520 X |
| 3,921,452 | 11/1975 | Sartorius | 73/343.5 |
| 4,117,340 | 9/1978 | Goto et al. | 364/520 X |

Primary Examiner—Edward J. Wise
Attorney, Agent, or Firm—Salvatore A. Giarratana; Francis L. Masselle; Edwin T. Grimes

[57] ABSTRACT

An apparatus for automatically scaling an X-Y recorder for use with a thermal analyser wherein temperature range span during an experiment may be plotted exactly scaled to an abscissa such that the left side of the graphical representation corresponds exactly to the minimum temperature during the experiment and the right side of the representation corresponds exactly to the maximum temperature achieved.

6 Claims, 2 Drawing Figures

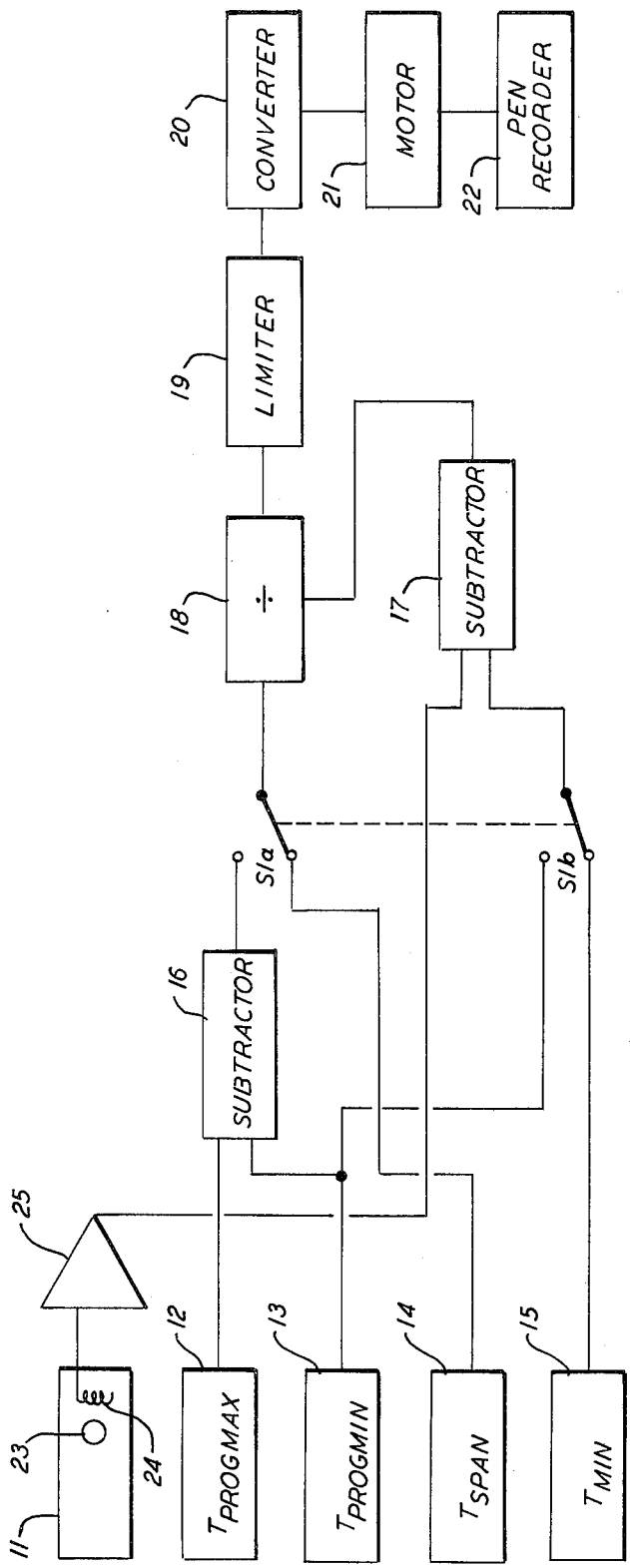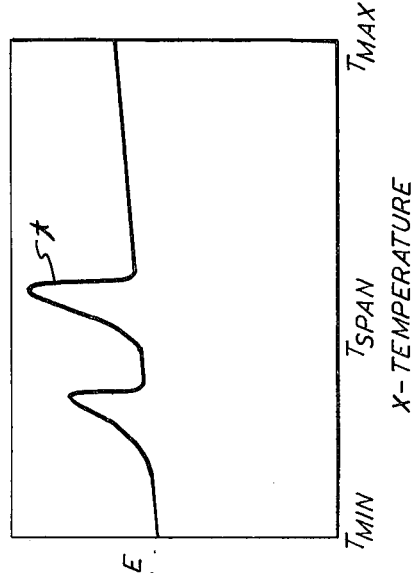

AUTOMATIC RECORDER ABSCISSA SCALING

BACKGROUND OF THE INVENTION

When a sample is examined through a temperature range in a thermal analyser, one method of exhibiting analytical results is by means of an X-Y recorder where the abscissa is representative of the temperature range through which the sample is subjected. The ordinate then gives an indication of the effect of the temperature on the particular property of the sample under investigation. To view this graphical representation in detail it is advantageous to scale the abscissa such that the temperature range spanned during an experiment is plotted exactly scaled to the pen recorder abscissa such that the left side of the graphical representation corresponds exactly to the minimum temperature reached during the experiment and the right side of the representation corresponds exactly to the maximum temperature reached or anticipated during the experiment. This permits observation of experimental results between the minimum and maximum temperatures of interest as opposed to a range of tempertures over which only a relatively small portion thereof are experimental results desired. Thus, an experimenter who is interested in observing phenomena over a relatively short temperature range may be forced to view the phenomena in a cramped small temperature range within a much larger temperature range represented by the abscissa. Thus, it is highly desirable to be able to select and expand throughout the entire available abscissa that temperature between a minimum temperature and a maximum temperature over which it is desired to observe experimental phenomena.

Heretofore, such adjustments have been done manually which requires that two or more adjustments be made on every occasion that a change is made in the limits between which the sample temperature is to be varied. A signal representative of the sample temperature must be subjected to two operations before being applied to the horizontal input of the pen recorder. An offset of a magnitude equivalent to the minimum temperature that the sample will attain must be subtracted such that when the sample is at this minimum temperature the resultant abscissa drive signal to the pen recorder is zero and the pen is therefore positioned at the left side of the paper. This adjusted signal must then be multiplied by a factor of magnitude equivalent to the full scale signal needed to position the pen recorder along the X axis to the right hand side of the paper divided by the temperature span to which the sample will be subjected. Therefore, the two adjustments necessary are offset and scaling operations. With a manual implementation, the operator must carefully and accurately make these adjustments every time a change of temperature range is made. Since these adjustments may be interactive, a time consuming repetitive procedure may be necessary.

The present invention contemplated apparatus for accurately and automatically making these corrections.

SUMMARY OF THE INVENTION

The apparatus of the present invention automatically drives the abscissa X axis of the pen recorder in an X-Y recorder with a signal representing temperature but with two adjustments (offset and scaling) automatically made so that when the sample is at the minimum temperature to be achieved, the pen carriage is to the left most position of the paper and when the sample is subjected to the highest temperature the pen is fully to the right of the record paper. This results in a graphical representation that is linearly and exactly scaled to match the graphical paper width to the temperature range to be spanned.

The present invention is operational in two modes.

The first mode is where an operator knows the minimum temperature and the temperature span through which the experiment on a sample is to be performed. In the second mode, the operator performs a thermal analysis from which the experimental result is already at least partly known and the result is to some extent predictable. Such a case could result in routine analyses of samples where the desired experimental result might be some quantative assessment of composition purity or the like of the sample. In such a situation, the temperature range to be spanned by the sample would normally be fixed and known from previous exploratory experiments. Thus, a temperature program could be entered into the temperature control arrangement before the commencement of the experiment. Once this program was correctly entered, a temperature control system would be caused to execute the program automatically and unattended by the operator who would initiate execution of the program which would then run to conclusion and halt pending the operator's return to evaluate the experimental results or whatever.

DESCRIPTION OF THE DRAWINGS

FIG. 1 illustrates in block diagram form a preferred embodiment of the present invention:

FIG. 2 represents the ordinate-abscissa relationship of a typical sheet used in a recorder of the present invention.

DESCRIPTION

Referring now to FIG. 1, there is shown the block diagram incorporating the two modes of the present invention, depending on the setting of switch S 1 which comprises switches S 1a and S 1b. If switch is S·1 is in the position shown, the system operates in the first mode.

An oven 11 contains a sample 23 representative of a sample on which a thermal experiment is to be performed. In the experiment the sample will be heated (by means not shown) through a temperature range. Changes in the property under investigation due to temperature will then be recorded as ordinate values on an X-Y recorder. The manner of generating the signal for driving the pen recorder in the ordinate direction is not part of this invention which is confined to the generation of an adjusted signal for driving the pen recorder in the X direction.

A thermocouple 24 is disposed adjacent the sample 23 and provides a signal proportional to the temperature of the sample to an amplifier 25 and then as an input signal to a subtractor circuit 17 representative of current sample temperature. A T MIN selector 15 is connected to subtractor 17 via switch S 1b. The input from T MIN selector 15 is an operator entered value for the minimum temperature to be obtained during the analysis (typically the initial temperature). A T span selector 14 is connected to a divider 18 via switch S 1a. The input from T span selector 14 is also an operator entered value for the temperature span to be traversed during the experiment. A conceptually similar alternative would be to enter the maximum expected temperature instead from which T span could be determined by subtraction. As aforesaid, the input from thermocouple 24 is a signal representing the current value of the experimental temperature. The subtractor 17 calculates the difference between current sample temperature represented by the input from thermocouple 24 and the selected minimum temperature representated by the input from T MIN selector 15. This difference is the offset temperature signal. The output of subtractor 17 provided as an input to divider 18. The divider 18 divides the difference signal from the subtractor 17 by the input from T span selector 14. The output of divider 18 is zero when the outputs from the amplifier 25 representative of current sample temperature and T MIN block 15 are equal and will be full scale when the output from the amplifier 25 is the same as the maximum temperature from which the temperature span was calculated. The output of divider 18 is essentially the required offset and scaled temperature signal to drive the abscissa of the pen recorder 22.

A limiter 19 is connected to divider 18 and acts as a limiting device which insures that if for any reason sample temperature falls below T MIN, the output from divider 18 is clamped to zero and not permitted to go negative. The limiter 19 also insures that if sample temperature for any reason exceeds the maximum temperature then the output of divider circuit 18 is clamped and not permitted to exceed a full scale. The output of limiting circuit 19 is connected to converter 20 which converts the offset, scale and clamped temperature signal into a form appropriate for the motor 21 and the pen recorder 22 being used.

If the present invention is implemented in analog form to drive an alalog pen recorder, then converter 20 would be a simple fixed gain amplifier to correct the full scale output to the full scale input voltage required by the pen recorder 22. If on the other hand, the invention is implemented in digital form to drive an analog pen recorder 22, then converter circuit 20 would be a digital to analog converter or alternately motor 21 could be a stepping motor driven via a digital amplifier.

In operation, if an operator is investigating the properties of a sample and is uncertain of the experimental results, he may wish to monitor the progress of the experiment and retain the option of innovating where necessary. In this case, he might want to command the heater system (not shown) to start heating at a given rate from a certain initial temperature with the intention of monitoring the phenomenon of interest. When a phenomenon has occurred he would then command the heater control to stop heating (or possibly to cool the apparatus prior to reheating the experiment, or removing the sample). Thus, the operator would know definitely at what temperature he wishes to commence the experiment but might know only roughly the maximum temperature to which he would need to continue the experiment. Therefore, the operator could specify a potential maximum temperature at which he could be sure the experiment would be complete but with the intention of terminating the experiment when the phenomenon of interest has occurred without continuing to the maximum temperature if unnecessary. Thus, by use of portion of FIG. 1 just described, this condition can be taken care of by providing the means whereby before commencing the experiment, the operator can enter into the heater controller the initial or a minimum temperature at which the experiment will commence together with the maximum temperature he can envision needing to be attained from which the temperature span can be determined. Thus, by means of the circuit just described in connection with FIG. 1, the operator can enter into the heater control system, the minimum temperature and the temperature span whereupon the circuit of FIG. 1 would make the necessary calculations to automatically offset and scale a signal derived from the sample temperature during analysis and use this to drive the abscissa of the pen recorder 22 to exactly match the horizontal span of the recorder with the intended temperature range as described above to make optimum use of the horizontal breadth of the graphic record of the experiment on the X-Y recorder.

When the switch is S 1a and S 1b are in the position opposite from shown, the two reference inputs to the system are provided by blocks 12 and 13 representing the minimum and maximum temperatures referenced in a temperature program and deduced and made available by a temperature program controller (not shown). The blocks 12 and 13 are connected to subtractor 16 which subtracts the programmed minimum and maximum sample temperatures. This difference is provided as an input to divider circuit 18 and since the output from block 13 is also provided as an input to subtractor 17, the difference between the outputs from the blocks 12 and 13 is divided by the output from the block 14 minus the output from the block 13. In a manner similar to that described above with respect to the first mode operation the recorder pen 22 is driven between a programmed T MIN and T MAX.

Since the inputs from blocks 12 and 13 are simply those preselected by a program made possible by prior knowledge of the temperature span over which the experiment is to be performed, the recording pen 22 is driven along the abscissa through positions appropriate to the offsets and scaled temperature signals.

The foregoing use of the program inputs is possible since the experimental results is partly known and the result to some extent predictable. Such a case could be the routine analysis of samples of some process where the desired experimental result might be some quantative assesment of composition purity or the like. In such a case temperature range to be spanned by the sample would, in general, be fixed and known from previous exploratory experiments. Thus, a temperature program could be entered into the temperature control electronics before the commencement of the experiment of measurement. Once this program was correctly entered, the temperature control electronics could be caused to execute the program automatically and unattended by the user who would initiate execution of the program which would then run to conclusion and halt of its own accord in the absence of the operator. For a complicated experiment or analysis such a temperature program could consist of several temperatures between which the sample would be varied at different heating and cooling rates possibly with isothermal pauses between periods of heating or cooling. The temperature control electronics would have entered full details of the temperature program to be executed and thereform directly calculated the minimum temperature and maximum temperatures without the operatur needing to explicitly or additionally enter them. Thus, in this second mode the temperature control electronics can upon completion of the entry of a temperature program compare the various temperatures referenced as part of the program and determine the minimum temperature to be obtained during execution of the program together with the difference between the minimum and maximum temperatures which is the temperature span. Thereafter during the execution of the temperature program, the temperature electronics can continuously offset the signal representing the current temperature with a signal representing the minimum temperature and then scaled as offset signal with a factor representing the temperature span and thereby generate a scaled offset signal to the abscissa axis of a pen recorder 22 to exactly match the temperature range to be spanned to the width of the paper as previously described. This enhanced scheme is an improvement upon the scheme previously described in reference to FIG. 1 in that the temperature control electronics automatically infer the minimum temperature and temperature span from the entered temperature program without the operator needing to calculate and enter these extra values. Also, if any part of the temperature program is later individually changed, the temperature control electronics automatically changes its inferred temperature minimum and temperature span without the operator needing to remember to calculate or enter them.

FIG. 2 illustrates a sheet of record paper where the graph traced in the X or horizontal direction is done by a recorder pen under control of the present invention. As may be seen, the trace begins at the far left side of the sheet which is coincident with T MIN and terminates at the far right coincident with T MAX. Thus, T MIN is offset and the trace is scaled through the width T span. The trace t whose Y migrations represent properties of the sample within the defined temperature range has its movement in the X direction controlled by the present invention, automatically taking up the entire width of the sheet.

Other modifications of the present invention are possible in light of the above description which should not be construed as limiting the invention other than as limited by the Claims which follow:

We claim:

1. In a thermal analysis system having an X-Y recorder for graphically displaying changes in sample properties through a temperature range,
    pen recorder means,
    drive means connected to said pen recorder means for driving said pen recorder in the X direction in response to changes in sample temperature,
    first means responsive to sample temperature to generate a signal proportional to sample temperature,
    second means connected between said drive means and first means for offsetting said signal to zero at preselected sample temperature and scaling said signal to be at its maximum when said sample temperature is at a preselected maximum.

2. In a thermal analysis system according to claim 1 wherein said first means comprises,
    thermocouple means disposed adjacent the sample providing a continuous signal proportional to sample temperature.

3. In a thermal analysis system according to claim 2 wherein said second means comprises,
    first subtractor means connected to said first means,
    third means connected to said first subtractor means providing an input representative of a preselected sample minimum temperature,
    divider means connected to receive the output of said first subtractor means,
    fourth means connected to said divider means providing an input representative of a preselected sample temperature span through which the sample is to be heated whereby said divider means provides an output signal proportional to the difference between said sample temperature and said preselected sample minimum temperature divided by said preselected temperature span.

4. In a thermal analysis system according to claim 3 including,
    clamping means connected between said divider and said drive means to clamp the output of said divider to zero if said sample temperature falls below said preselected sample minimum temperature and at the maximum sample temperature defined by said preselected sample temperature span if said sample temperature exceeds said maximum sample temperature.

5. In a thermal analysis system according to claim 4 including
    fifth means providing an output representative of a maximum sample temperature,
    sixth means providing an output representative of a minimum sample temperature,
    second subtractor means connected to said fifth and sixth means providing an output proportional to the difference said maximum and minimum sample temperature,
    switch means for connecting said second subtractor to said divider means and said sixth means to said first subtractor means.

6. In a thermal analysis system according to claim 5 said switch means comprises,
    a first switch having a first position connecting said fourth means to said divider means and a second position connecting said second subtractor means to said divider means,
    a second switch operable only in tandem with said first switch connecting said sixth means to said first subtractor means in said second position and said third means to said first subtractor means when in said first position.

* * * * *

UNITED STATES PATENT AND TRADEMARK OFFICE
CERTIFICATE OF CORRECTION

PATENT NO. : 4,246,640
DATED : January 20, 1981
INVENTOR(S) : Simon Babil et al.

It is certified that error appears in the above-identified patent and that said Letters Patent are hereby corrected as shown below:

Column 1, line 58, change "contemplated" to --contemplates--.

Column 3, line 7, change "representated" to --represented--.

Column 3, line 9, change "subtractor 17 provided" to --subtractor 17 is provided--.

Column 3, line 33, change "alalog" to --analog--.

Column 4, line 13, change "switch is" to --switches--.

Column 4, line 41, change "assesment" to --assessment--.

Column 4, line 59, change "thereform" to --therefrom--.

Column 4, line 61, change "operatur" to --operator--.

Column 4, line 62, change "explicidly" to --explicitly--.

Column 6, line 31, change "including" to --including,--.

Column 6, line 38, change "difference said" to --difference between said--.

Signed and Sealed this

Twelfth Day of October 1982

[SEAL]

Attest:

GERALD J. MOSSINGHOFF

Attesting Officer    Commissioner of Patents and Trademarks